(12) United States Patent
Bille

(10) Patent No.: US 8,650,018 B2
(45) Date of Patent: Feb. 11, 2014

(54) SYSTEM AND METHOD FOR ASSESSING RISK OF GLAUCOMA ONSET

(75) Inventor: Josef F. Bille, Heidelberg (DE)

(73) Assignee: Heidelberg Engineering GmbH, Heidelberg (DE)

( * ) Notice: Subject to any disclaimer, the term of this patent is extended or adjusted under 35 U.S.C. 154(b) by 131 days.

(21) Appl. No.: 13/371,122

(22) Filed: Feb. 10, 2012

(65) Prior Publication Data

US 2012/0143035 A1 Jun. 7, 2012

Related U.S. Application Data

(62) Division of application No. 12/397,954, filed on Mar. 4, 2009, now Pat. No. 8,137,271.

(51) Int. Cl.
*G06G 7/58* (2006.01)
*A61B 3/16* (2006.01)

(52) U.S. Cl.
USPC .................................... 703/11; 600/398

(58) Field of Classification Search
USPC .............. 600/398–405; 702/138, 139; 703/11
See application file for complete search history.

(56) References Cited

U.S. PATENT DOCUMENTS

| | | | | |
|---|---|---|---|---|
| 4,579,430 A | * | 4/1986 | Bille | 351/206 |
| 4,838,679 A | * | 6/1989 | Bille | 351/205 |
| 5,062,702 A | * | 11/1991 | Bille | 351/212 |
| 5,777,719 A | * | 7/1998 | Williams et al. | 351/212 |
| 2004/0054358 A1 | * | 3/2004 | Cox et al. | 606/5 |

FOREIGN PATENT DOCUMENTS

WO  WO 0195790 A1 * 12/2001

OTHER PUBLICATIONS

Ian A. Sigal, et al., "Modeling individual-specific human optic nerve head biomechanics. Part I: IOP-induced deformations and influence of geometry" Biomechanics and Modeling in Mechanobiology, Feb. 29, 2008, pp. 85-98, vol. 8, No. 2, Springer, Berlin, DE.*

Ruiz, "Preliminary clinical results of non-invasive intrastromal correction of presbyopia using the FEMTEC femtosecond laser system," Centro Oftalmologico Colombiano, Bogota, article presented at Hawaiian Eye Meeting 2008, Jan. 23, 2008.*

* cited by examiner

*Primary Examiner* — Brian Szmal
(74) *Attorney, Agent, or Firm* — Nydegger & Associates

(57) ABSTRACT

A system and method for predicting the onset of glaucoma uses a Finite Element Model (FEM) to obtain a response profile of the Optical Nerve Head (ONH) inside an eye. To do this, the FEM is programmed with data from first and second images of the ONH that are respectively taken at the beginning and the end of an imposed pressure differential (e.g. over a range of about 8kPa). The FEM is then subjected to a sequence of pressure increments and the resultant profile is compared with empirical data to predict an onset of glaucoma.

6 Claims, 1 Drawing Sheet

SYSTEM AND METHOD FOR ASSESSING RISK OF GLAUCOMA ONSET

This application is a divisional of application Ser. No. 12/397,954, filed Mar. 4, 2009, which is currently pending. The contents of application Ser. No. 12/397,954 are incorporated herein by reference.

FIELD OF THE INVENTION

The present invention pertains generally to ophthalmic diagnostic systems and methods for their use. More particularly, the present invention pertains to systems and methods that are used to predict the onset of glaucoma before symptoms of the disease become apparent. The present invention is particularly, but not exclusively, useful as a system or method for using a Finite Element Model (FEM) to predict the onset of glaucoma.

BACKGROUND OF THE INVENTION

Glaucoma is a medical condition where increased pressure within an eyeball causes a gradual loss of sight. Although glaucoma can not be cured, if detected early enough it can be controlled by medications, surgery, or both. In any case, the important thing is to have early detection. In the early stages of the disease, however, there are few detectable symptoms that are glaucoma specific. Nevertheless, there are certain risk factors, such as age, race, and family history, in addition to hypertension, which can indicate that an early detection (prediction) of glaucoma may be prudent. Stated differently, it may be desirable to identify candidates early on for the pharmacological treatment of glaucoma. And, consequently, to thereby determine a properly required pharmacological regimen, including the type and strength of medications to be used.

It is known that an increased intraocular pressure (IOP) inside the eyeball causes glaucoma. An increased IOP also causes noticeable anatomical changes in the eye. In particular, as a consequence of the increased IOP, changes in biomechanical stress conditions in the Lamina Cribrosa (LC) of the Optical Nerve Head (ONH) are observable. Importantly, these observations can be evaluated to determine whether any damage to the LC is due to an increase in IOP. If so, glaucoma may be indicated. On the other hand, a healthy eye, without glaucoma, will resist the cell damage that would otherwise be caused by an increase in IOP.

Anatomically, the LC is generally a cylindrical-shaped, mesh-like structure that includes pores which pass through the structure. It is located at the back of an eye, and is positioned in a hole through the sclera at the ONH where fibers of the optic nerve exit the eye. In addition to supporting these nerve fibers, it is believed that an important function of the LC is to help maintain an appropriate pressure gradient between the inside of the eye (i.e. IOP) and the surrounding tissue. For this purpose, the LC is more sensitive to pressure differences than is the thicker, denser sclera surrounding the ONH. Consequently, it tends toward a measurable change in its configuration with increased IOP. Importantly, it is believed that configuration changes in the LC contribute to glaucoma.

Mathematical models of anatomical structures, such as components of the eye, can be very helpful diagnostic tools. In particular, whenever an anatomical structure is somehow forced to change, a Finite Element Model (FEM) is known to be helpful for evaluating the consequences of the change. For example, U.S. patent application Ser. No. 12/205,420 for an invention entitled "Finite Element Model of a Keratoconic Cornea" which is assigned to the same assignee as the present invention, discloses a mathematical methodology for predicting the condition of an eye in response to a proposed surgical procedure.

In light of the above, it is an object of the present invention to provide a system and method for predicting the onset of glaucoma before symptoms of the disease become apparent. Another object of the present invention is to identify candidates for the pharmacological treatment of glaucoma, and to provide information for subsequently establishing the treatment regimen. Yet another object of the present invention is to provide a system and method for mathematically modeling the Lamina Cribrosa (LC) to create a pressure response profile for comparison with empirical data to predict the onset of glaucoma. Still another object of the present invention is to provide a system and method for predicting the onset of glaucoma that is easy to implement, is simple to use and is comparatively cost effective.

SUMMARY OF THE INVENTION

In accordance with the present invention, a system and method for diagnosing the onset of glaucoma in an eye involves evaluating anatomical parameters under various pressure conditions. More specifically, the parameters to be evaluated are associated with tissue of the Optical Nerve Head (ONH) in the eye. For this evaluation, the present invention relies on the use of a Finite Element Model (FEM) that replicates the ONH. In particular, this evaluation is based on the comparison of an empirical statistic with a profile that is generated by the FEM in response to a simulated pressure differential.

In detail, the FEM comprises a plurality of mathematical tensor elements, with each individual element representing anatomical tissue at a particular location on the ONH. Structurally, the FEM substantially replicates the ONH as a cylindrical shaped body having a first end surface and a second end surface, with a cylindrical surface extending between the peripheries of the two end surfaces. For this configuration, tensor elements of the FEM representing the Prelaminar Neural Tissue (PrNT) are arranged on the first end surface. Elements representing Postlaminar Neural Tissue (PoNT) are arranged on the second end surface. And, between the PrNT and the PoNT, tensor elements representing the Lamina Cribrosa (LC) are located inside the cylinder shape. Also, tensor elements of the FEM representing the sclera are arranged on the cylindrical surface. Further, these sclera elements include a plurality of fiber elements that transition in an outward direction from a substantially circumferential orientation at the cylindrical surface to an increasingly spiral orientation with increasing distance from the cylindrical surface. This is done to add stability to the FEM.

In operation, anatomical data is obtained from a patient for use in programming the FEM. More specifically, this acquisition of data is done in two steps. First, stress-strain measurements (data) are taken from the ONH when the eye is under a first pressure (e.g. 2 kPa). This creates a first image of the ONH. Second, the procedure is repeated to obtain stress-strain measurements (data) when the eye is under a second pressure (e.g. 8 kPa). This creates a second image of the ONH. Data from the first and second images are then programmed into the FEM.

Once the FEM has been programmed with the first and second images of the ONH, the tensor, parameters of the FEM are varied from a base condition (e.g. the first image) to obtain a profile of the ONH. Preferably, this variation covers a range of pressures (e.g. range of 8 kPa) and is done in a sequence of pressure increments, with each increment being approximately 1 kPa. The resultant profile is then compared with empirical data to predict an onset of glaucoma.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
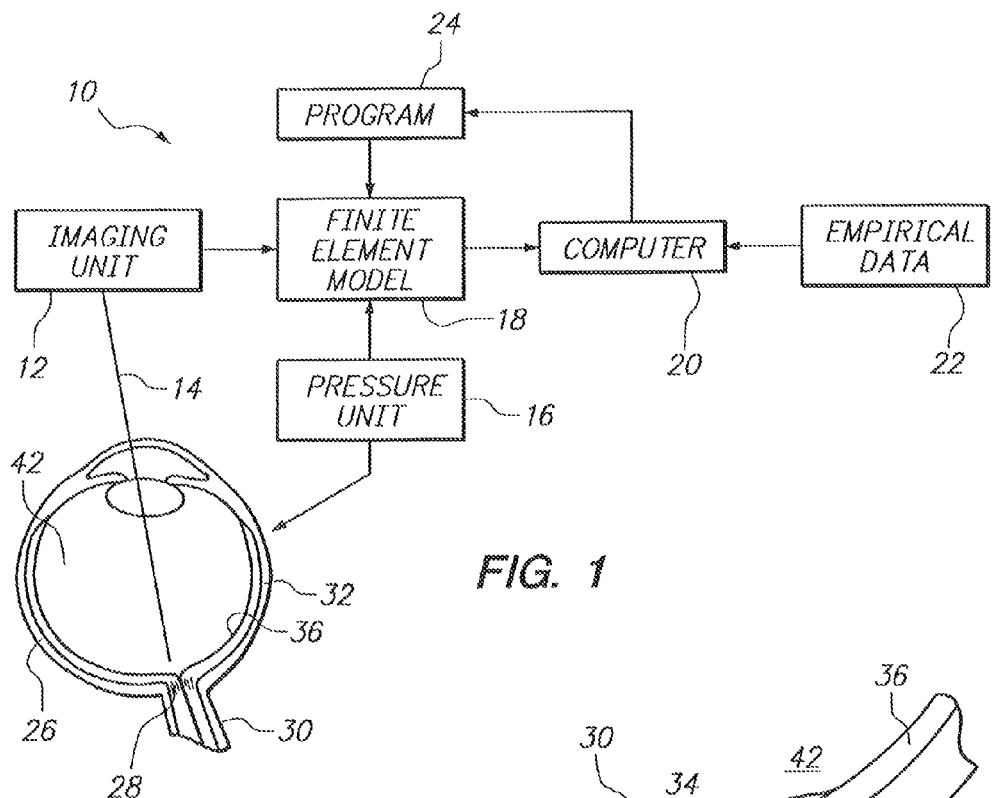
FIG. 1 is a schematic of the system of the present invention shown in its relationship with an eye (shown in cross section)

Referring initially to FIG. 1, a system for use with the present invention is shown and is generally designated 10. As shown, the system 10 includes an imaging unit 12 that has an illumination means (not shown) for directing light along a beam path 14. Further, the system 10 includes a pressure unit 16, and FIG. 1 shows that both the imaging unit 12 and the pressure unit 16 provide input for creation of a mathematical Finite Element Model (FEM) 18.

A computer 20 is shown in FIG. 1 with connections to both the FEM 18 and a database 22. As one of its functions, the computer 20 is used in the system 10 to run a program 24 for an operation of the FEM 18. More specifically, the program 24 subjects the FEM 18 to incremental pressure increases that simulate the progress of glaucoma. For another function, the computer 20 is used to compare the output from the FEM 18 with empirical data from a database 22. Thus, the input from the FEM 18 to the computer 20 is a consequence of the program 24. On the other hand, input from the database 22 to the computer 20 is empirical data that has been clinically collected from a plethora of different patients.

As is appreciated with reference to FIG. 1, the system 10 is intended for use in evaluating an eye 26. More specifically, the system 10 is to be used for evaluating the Lamina Cribrosa (LC) 28 that is located in the Optical Nerve Head (ONH) 30 of the eye 26. The anatomical aspects of the ONH 30 and the LC 28 as they pertain to the present invention will be best appreciated with reference to FIG. 2.

Figure 2:
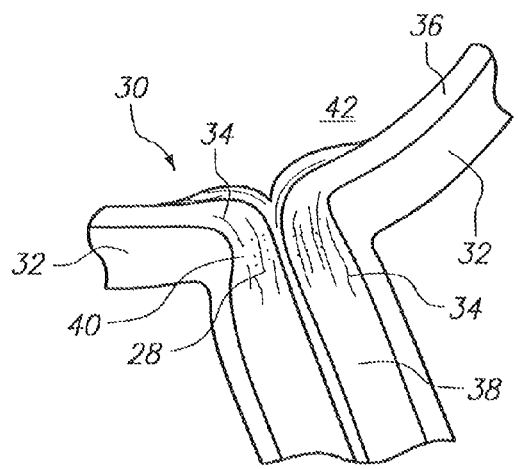
FIG. 2 is an enlarged view of the Lamina Cribrosa (LC), and the Optical Nerve Head (ONH) of the eye shown in FIG. 1.

In FIG. 2 it will be seen that the LC 28 is surrounded by sclera 32, and includes nerve fibers 34 that extend from the retina 36 as they exit from the eye 26 and into the optic nerve 38. Further, the LC 28 is a mesh-like structure that includes a plurality of pores 40. Functionally, the LC 28 is continuously subjected to intraocular pressure from the vitreous body 42 of the eye 26. An FEM 18 that mathematically replicates the LC 28 is shown in FIG. 3.

Figure 3:
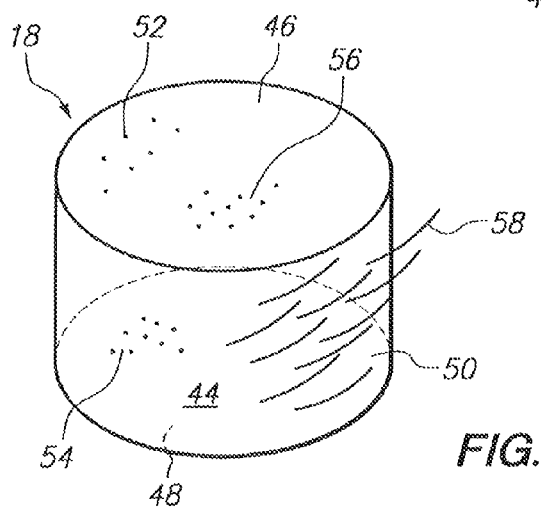
FIG. 3 is a perspective view of a Finite Element Model presented as a mathematical representation of the LC for use with the present invention.

FIG. 3 shows that a FEM 18 for mathematically representing the LC 28 substantially replicates a cylindrical shaped body 44. As such the body 44 has a first end surface 46 and a second end surface 48, with a cylindrical surface 50 that extends between the end surfaces 46 and 48 to represent the periphery of the LC 28. As intended for the present invention, the first end surface 46 of the body 44 is used to replicate the location of Prelaminar Neural Tissue (PrNT) of the LC 28. And, similarly, the second end surface 48 of the body 44 is used to replicate the location of Postlaminar Neural Tissue (PoNT) of the LC 28.

For the mathematical aspects of the FEM 18, a plethora of elements 52 are arranged over the first end surface 46 of the body 44 for this purpose (Note: the elements 52 shown in FIG. 3 are only exemplary). Also, a plethora of elements 54 (also exemplary) are arranged on the second end surface. Between the end surfaces 46 and 48, and within the body 44, are elements 56 of the FEM 18 that represent the LC 28 itself. Further, fiber elements 58 that represent the sclera 32 are arranged on the cylindrical surface 50 of the FEM 18. More specifically, these fiber elements 58 are arranged to transition in an outward direction from the cylindrical surface 50 with a transition characterized by a change from a substantially circumferential orientation at the cylindrical surface 50 to an increasingly spiral orientation with increasing distance from the cylindrical surface 50. The purpose here is to replicate the stability provided by the sclera 32 for the LC 28. As will be appreciated by the skilled artisan, each of the elements 52, 54, 56 and 58 in the FEM 18 are mathematical tensors that can be individually programmed to represent biomechanical properties of tissue at a location in the anatomical structure being replicated.

OPERATION

In the operation of the system 10 of the present invention, an eye 26 that is to be evaluated is subjected to a pressure differential by the pressure unit 16. More specifically, this pressure differential will preferably be over a range of about 8 kPa. First, the eye 26 is subjected to an initial pressure (e.g. 2 kPa). With eye 26 under this initial pressure, the imaging unit 12 is employed to create an image of the LC 28. In detail, this imaging can involve well known techniques that include the use of confocal microscopy or Optical Coherence Tomography (OCT) for general imaging. It can also involve Second Harmonic Generation (SHG) imaging for determining micromorphology parameters. For instance, the location and sizes of pores 40 in the LC 28 may be best determined by SHG imaging. In any event, these imaging techniques are employed to obtain measurable data concerning biomechanical stress/strain parameters of tissue in the LC 28. Next, the eye 26 is subjected to a subsequent pressure (e.g. 10 kPa) by the pressure unit 16. Again, while the eye 26 is under this subsequent pressure, images of the LC 28 are made and biomechanical stress/strain parameters of tissue in the LC 28 of the eye 26 are taken. All of this information is then used to program the FEM 18.

Once the FEM 18 has been programmed with biomechanical stress/strain parameters taken from the eye 26, the FEM 18 is manipulated through a sequence of pressure increments. More specifically, the FEM 18 is first observed at a base pressure, and is then subsequently observed at increased pressure levels. These levels will typically be at intervals of about 1 kPa. During this process, changes in the tensor parameters of the elements 52, 54, 56 and 58 are observed at each pressure level, and are recorded to create a pressure response profile for the eye 26.

As indicated in FIG. 1, the pressure response profile that is created as disclosed above is provided as input to the computer 20. The computer 20 is then used to compare the pressure response profile with empirical data retrieved from the database 22. In accordance with this comparison, it can then be determined whether the eye 26 is a glaucoma candidate that should receive pharmacological treatment.

While the particular System and Method for Assessing Risk of Glaucoma Onset as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for determining the onset of glaucoma which comprises the steps of:
    using an imaging unit to create a first image of an Optical Nerve Head (ONH) of a patient at a first pressure;
    using the imaging unit to create a second image of the ONH at a second pressure established by a pressure unit;
    using a computer programmed to assess the first image and the second image to establish data of stress-strain characteristics for tissue of the ONH at each of a plurality of locations in the ONH;
    programming a Finite Element Model (FEM) of an ONH with the data established in the assessing step, the FEM having elements respectively representative of a Lamina Cribrosa (LC), Prelaminar Neural Tissue (PrNT), Post-laminar Neural Tissue (PoNT), and Sclera, wherein each element of the FEM is defined by mathematical parameters based on the data;
    varying parameters of the FEM to obtain a profile for the ONH of the patient; and
    evaluating the profile in comparison with empirical statistics to predict an onset of glaucoma.

2. A method as recited in claim 1 wherein the profile is obtained from a plurality of simulated pressure changes on the FEM, wherein the pressure changes are made through a range of 8 kPa, with each pressure change resulting from a pressure increment equal to 1 kPa.

3. A method as recited in claim 1 wherein the first image is created at a pressure of 2 kPa and the second image is created at a pressure of 8 kPa.

4. A method as recited in claim 1 wherein the FEM replicates a cylindrical shaped body having a first end surface and a second end surface with a cylindrical surface therebetween, and further wherein elements of the FEM representing the PrNT are arranged on the first end surface, elements of the FEM representing the PoNT are arranged on the second end surface, elements of the FEM representing the LC are located between the first end surface and the second end surface, and elements of the FEM representing the sclera are arranged on the cylindrical surface.

5. A method as recited in claim 4 wherein the elements of the FEM representing the sclera include a plurality of fiber elements, with the fiber elements transitioning in an outward direction from the cylindrical surface, with the transition being characterized by a change from a circumferential orientation at the cylindrical surface to an increasingly spiral orientation with increasing distance from the cylindrical surface, to add stability to the FEM.

6. A method as recited in claim 5 wherein the elements of the FEM representing the LC include simulated pores, wherein a location and a size for each pore is determined by Second Harmonic Generation (SHG) imaging of the ONH.

* * * * *